(12) United States Patent
Dean

(10) Patent No.: US 9,223,863 B2
(45) Date of Patent: *Dec. 29, 2015

(54) DETECTION OF CONDITIONS FROM SOUND

(71) Applicant: Dean Enterprises, LLC, Kennesaw, GA (US)

(72) Inventor: Vickie A. Dean, Locust Grove, GA (US)

(73) Assignee: Dean Enterprises, LLC, Locust Grove, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,416

(22) Filed: Dec. 5, 2012

(65) Prior Publication Data

US 2013/0096844 A1  Apr. 18, 2013

Related U.S. Application Data

(63) Continuation of application No. 12/339,445, filed on Dec. 19, 2008, now Pat. No. 8,346,559.

(60) Provisional application No. 61/015,535, filed on Dec. 20, 2007.

(51) Int. Cl.

| G10L 21/00 | (2013.01) |
| G06F 17/30 | (2006.01) |
| A61B 5/16 | (2006.01) |
| A61B 5/00 | (2006.01) |
| G10L 17/26 | (2013.01) |

(52) U.S. Cl.
CPC .......... *G06F 17/30743* (2013.01); *A61B 5/16* (2013.01); *A61B 5/411* (2013.01); *A61B 5/4803* (2013.01); *G10L 17/26* (2013.01)

(58) Field of Classification Search
CPC ....... G10L 17/005; G10L 17/22; G06F 21/32; G07C 9/00158; G07C 9/00166
USPC .......................................................... 704/243
See application file for complete search history.

(56) References Cited

U.S. PATENT DOCUMENTS

| 3,588,363 | A |   | 6/1971  | Herscher |           |
|-----------|---|---|---------|----------|-----------|
| 3,619,509 | A | * | 11/1971 | Barger et al. | 704/250 |
| 3,743,783 | A |   | 7/1973  | Agnello  |           |
| 4,093,821 | A | * | 6/1978  | Williamson | 704/207 |
| 4,428,381 | A | * | 1/1984  | Hepp     | 600/528   |
| 4,458,693 | A | * | 7/1984  | Badzinski et al. | 600/528 |
| 5,148,483 | A |   | 9/1992  | Silverman et al. |     |
| 5,539,860 | A | * | 7/1996  | DeSimone et al. | 704/234 |

(Continued)

OTHER PUBLICATIONS

Dean, Vickie, "Sona Soma: Symphony of the Soul," Informational pamphlet by Vocal Images, 2001, US, 35 pages.

(Continued)

*Primary Examiner* — Pierre-Louis Desir
*Assistant Examiner* — Fariba Sirjani

(57) ABSTRACT

Disclosed are various systems, methods, and programs embodied in a computer-readable medium for sound analysis. The sound analysis involves transforming a sound print into a frequency domain in a memory to generate a frequency spectrum. A plurality of signatures are identified in the frequency spectrum. Also, a plurality of frequency ranges associated with the signatures are identified in the sound print. The frequencies associated with a physiological profile are cross-referenced with the frequency ranges to determine if the physiological profile is applicable to the sound print.

20 Claims, 14 Drawing Sheets

(56) References Cited

U.S. PATENT DOCUMENTS

| | | | |
|---|---|---|---|
| 5,675,705 A | 10/1997 | Singhal et al. | |
| 5,776,055 A * | 7/1998 | Hayre | 600/300 |
| 5,796,924 A * | 8/1998 | Errico et al. | 706/25 |
| 6,006,188 A | 12/1999 | Bogdashevsky et al. | |
| 6,055,501 A | 4/2000 | MacCaughelty | |
| 6,057,502 A | 5/2000 | Fujishima | |
| 6,118,104 A * | 9/2000 | Berkcan et al. | 219/494 |
| 6,141,637 A | 10/2000 | Kondo | |
| 6,151,571 A | 11/2000 | Pertrushin | |
| 6,289,313 B1 | 9/2001 | Heinonen et al. | |
| 6,363,346 B1 | 3/2002 | Walters | |
| 6,375,623 B1 * | 4/2002 | Gavriely | 600/534 |
| 6,436,057 B1 * | 8/2002 | Goldsmith et al. | 600/586 |
| 6,484,044 B1 * | 11/2002 | Lilienfeld-Toal | 600/316 |
| 6,496,115 B2 | 12/2002 | Arakawa | |
| 6,507,790 B1 * | 1/2003 | Radomski | 702/39 |
| 6,523,008 B1 | 2/2003 | Avrunin et al. | |
| 6,638,217 B1 | 10/2003 | Liberman | |
| 6,766,328 B2 | 7/2004 | Stefanchik et al. | |
| 6,839,581 B1 * | 1/2005 | El-Solh et al. | 600/324 |
| 7,062,443 B2 | 6/2006 | Silverman et al. | |
| 7,069,218 B2 | 6/2006 | Gordon | |
| 7,092,874 B2 | 8/2006 | Clavbo | |
| 7,165,033 B1 | 1/2007 | Liberman | |
| 7,174,203 B2 * | 2/2007 | Arand et al. | 600/513 |
| 7,190,795 B2 | 3/2007 | Simon | |
| 7,191,134 B2 | 3/2007 | Nunally | |
| 7,207,948 B2 * | 4/2007 | Coyle | 600/538 |
| 7,272,559 B1 * | 9/2007 | Hayre | 704/236 |
| 7,280,874 B2 | 10/2007 | Boehm | |
| 7,283,962 B2 * | 10/2007 | Meyerhoff et al. | 704/270 |
| 7,315,821 B2 * | 1/2008 | Monchi et al. | 704/273 |
| 7,416,531 B2 * | 8/2008 | Mohler | 600/528 |
| 7,571,101 B2 * | 8/2009 | Humble | 704/273 |
| 7,606,701 B2 | 10/2009 | Degani et al. | |
| 7,711,123 B2 * | 5/2010 | Crockett | 381/56 |
| 7,729,533 B2 * | 6/2010 | Sathyanarayana | 382/159 |
| 7,806,825 B2 * | 10/2010 | Heim | 600/453 |
| 7,809,554 B2 * | 10/2010 | Oh | 704/208 |
| 7,917,366 B1 * | 3/2011 | Levanon et al. | 704/270 |
| 7,981,045 B2 * | 7/2011 | Suzuki et al. | 600/529 |
| 8,066,647 B2 * | 11/2011 | Armitstead | 600/529 |
| 8,335,559 B2 * | 12/2012 | Tan et al. | 600/509 |
| 8,346,559 B2 * | 1/2013 | Dean | 704/270 |
| 2002/0077825 A1 | 6/2002 | Silverman et al. | |
| 2002/0138271 A1 | 9/2002 | Shaw | |
| 2002/0140714 A1 | 10/2002 | Hoffman | |
| 2002/0143242 A1 * | 10/2002 | Nemirovski | 600/300 |
| 2003/0028121 A1 * | 2/2003 | Blazey et al. | 600/549 |
| 2003/0028385 A1 | 2/2003 | Christodoulou | |
| 2003/0163299 A1 | 8/2003 | Iliff | |
| 2003/0182116 A1 | 9/2003 | Nunally | |
| 2003/0182117 A1 | 9/2003 | Monchi et al. | |
| 2004/0002853 A1 | 1/2004 | Clavbo | |
| 2004/0059570 A1 * | 3/2004 | Mochinaga et al. | 704/205 |
| 2004/0109571 A1 * | 6/2004 | Yoshimine | 381/67 |
| 2004/0243401 A1 | 12/2004 | Shiomi et al. | |
| 2004/0249634 A1 | 12/2004 | Degani et al. | |
| 2004/0267574 A1 | 12/2004 | Stefanchik et al. | |
| 2005/0131692 A1 | 6/2005 | Charles | |
| 2005/0187916 A1 * | 8/2005 | Levin et al. | 707/3 |
| 2005/0222515 A1 * | 10/2005 | Polyshchuk et al. | 600/528 |
| 2006/0015340 A1 | 1/2006 | Feng | |
| 2006/0036440 A1 * | 2/2006 | Kunkel | 704/270 |
| 2006/0198533 A1 * | 9/2006 | Wang et al. | 381/67 |
| 2006/0253278 A1 | 11/2006 | Furst-Yust | |
| 2007/0157224 A1 | 7/2007 | Pouliot et al. | |
| 2007/0213981 A1 * | 9/2007 | Meyerhoff et al. | 704/243 |
| 2007/0255563 A1 * | 11/2007 | Dooley | 704/236 |
| 2007/0271223 A1 * | 11/2007 | Zhang et al. | 707/2 |
| 2008/0040116 A1 | 2/2008 | Cronin et al. | |
| 2008/0045805 A1 * | 2/2008 | Sarel et al. | 600/300 |
| 2008/0063265 A1 * | 3/2008 | Sathyanarayana | 382/159 |
| 2008/0177195 A1 * | 7/2008 | Armitstead | 600/529 |
| 2008/0300867 A1 * | 12/2008 | Yan | 704/207 |
| 2009/0043586 A1 * | 2/2009 | MacAuslan | 704/270 |
| 2009/0092265 A1 | 4/2009 | Lovejoy | |
| 2012/0016252 A1 * | 1/2012 | Melker et al. | 600/532 |
| 2012/0033863 A1 * | 2/2012 | Wojton et al. | 382/128 |
| 2012/0088992 A1 * | 4/2012 | Armitstead | 600/323 |

OTHER PUBLICATIONS

Dean, V., et al., "Vocal Imaging," informational pamphlet by Vocal Images, USA, 15 pages (2001).

International Search Report and Written Opinion for International Application No. PCT/US2008/087564 mailed Mar. 4, 2009, 10 pages.

Meyer, W.L. et al., "A Summary of Sound Therapy and Vibrational Healing Concepts Book I," selected excerpts downloaded from http://www.healingsounds.com, Dec. 2003, Cover page, Acknowledgement page and pp. A1-A10, B1-B12, C1-C5, F1-F29.

* cited by examiner

FIG. 5

| | | Freq. Band 1 | Freq. Band 2 | Freq. Band 3 | Freq. Band 4 | Freq. Band 5 | Freq. Band 6 | Freq. Band 7 | Freq. Band 8 | Freq. Band 9 | Freq. Band 10 |
|---|---|---|---|---|---|---|---|---|---|---|---|
| Voice Print 1 | Octave 1 | 1 | 0 | 1 | 1 | 0 | 1 | 0 | 0 | 1 | 1 |
| | Octave 2 | 1 | 0 | 1 | 1 | 0 | 1 | 0 | 0 | 1 | 1 |
| | Octave 3 | 0 | 0 | 1 | 0 | 1 | 0 | 0 | 1 | 0 | 1 |
| Voice Print 2 | Octave 1 | 0 | 1 | 0 | 1 | 0 | 1 | 0 | 1 | 1 | 0 |
| | Octave 2 | 1 | 1 | 1 | 1 | 0 | 1 | 0 | 1 | 1 | 1 |
| | Octave 3 | 0 | 1 | 0 | 0 | 1 | 1 | 0 | 0 | 1 | 0 |
| Voice Print 3 | Octave 1 | 1 | 1 | 1 | 1 | 0 | 1 | 0 | 1 | 0 | 0 |
| | Octave 2 | 1 | 1 | 1 | 0 | 1 | 1 | 1 | 1 | 1 | 0 |
| | Octave 3 | 1 | 1 | 1 | 0 | 1 | 1 | 0 | 1 | 1 | 0 |
| Total Hits | | 6 | 6 | 7 | 5 | 4 | 8 | 1 | 6 | 7 | 4 |

FIG. 6

| | Freq. Band 1 | Freq. Band 2 | Freq. Band 3 | Freq. Band 4 | Freq. Band 5 | Freq. Band 6 | Freq. Band 7 | Freq. Band 8 | Freq. Band 9 | Freq. Band 10 |
|---|---|---|---|---|---|---|---|---|---|---|
| Total Hits | 6 | 6 | 7 | 5 | 4 | 8 | 1 | 6 | 7 | 4 |
| Greater than threshold of 5? | T | T | T | F | F | T | F | T | T | F |

| Substance | Profiles | Frequency | Category |
|---|---|---|---|
| Tibial m. anterior | foot | 14 | foot |
| Probable hemoglobin | influenza | 14.00024 | viral |
| Balantidium coli cysts | | 14.00146 | paracites |
| Uranium der | | 14.00172 | derivative |
| Tolloid-like protein 1 precursor | | 14.00256 | prot-sktal |
| Benzenthonium Chloride | chemical | 14.00277 | chemical |
| Nitrogren der | Nitrogen imbalance | 14.00307 | derivative |
| Matrix metalloproteinase-19 | Rheumatoid arthritis | 14.00317 | enzyme |
| Neonder | | 14.00606 | derivative |
| Nitrogren | Additional Trace Mineral | 14.007 | element |
| MYH11 protein | | 14.00708 | protein |
| Neurokinin-2 receptor | | 14.00781 | protein |
| Puberulonic Acid | | 14.00791 | bacteria |
| Oxygen der | Oxygen imbalance | 14.0086 | derivative |
| Zinc nitride | | 14.01147 | chemical |
| Serine/threonine-protein phosphatase | | 14.01196 | biochem |
| Astragalin | | 14.01198 | herbal |
| Cytochrome P450 | | 14.01221 | enzyme |
| Propantheline bromide | | 14.0125 | pharm |
| Fibroblast growth factor | lung functioning | 14.0127 | protein |
| Collagenase B~ | Rheumatoid arthritis | 14.01367 | biochem |
| Tomatidine | | 14.01367 | enzyme |
| Truncated non-neuronal | Central Nervous System | 14.01563 | protein |
| Acrolein | | 14.01604 | chemical |
| Parasorbic acid | | 14.01604 | botanical |
| Sorbic acid | | 14.01604 | organic |
| Allotetrahydrocortisone Diacetate | | 14.0174 | hormone |

159 — Substance column; 166 — Profiles column; 163 — Frequency column; 169 — Category column; 156 — Filtered Frequency Bands

FIG. 8

| Profile Name | Substance | Frequency | Recurrence & Importance |
|---|---|---|---|
| Parkinson's Disease | Cytochrome c oxidase polypeptide VIIa-liv | 18.3515625 | 99 |
| Parkinson's Disease | Abamectin - 3FORMS | 18.0165 | 88 |
| Parkinson's Disease | Antimycin A1 | 17.1448025 | 66 |
| Parkinson's Disease | Asparagine (L) | 16.5149 | 77 |
| Parkinson's Disease | Aspartic Acid, Ferrous Salt Tetrahydrate | 24.506255 | 99 |
| Parkinson's Disease | a-tocopherol | 26.919675 | 77 |
| Parkinson's Disease | Benserazide | 16.077895 | 99 |
| Parkinson's Disease | Bovine neurotensin triacetate hexahydrate | 17.85906281 | 88 |
| Parkinson's Disease | Calcium sulphate | 17.0177 | 88 |
| Parkinson's Disease | Chrysene | 14.26833 | 77 |
| Parkinson's Disease | Diethylaminoethanol (2-) | 14.648905 | 99 |
| Parkinson's Disease | Dopa | 24.648835 | 66 |
| Parkinson's Disease | Erythropoietin-alpha | 14.84375 | 88 |
| Parkinson's Disease | Glutathione (L) | 19.207975 | 66 |
| Parkinson's Disease | Glutathione (L) Disulfide | 19.14497875 | 67 |
| Parkinson's Disease | Glycine | 18.76681 | 99 |
| Parkinson's Disease | Glycine (L) HCl | 27.88197 | 77 |
| Parkinson's Disease | Human CNTF~ | 22.4609375 | 99 |
| Parkinson's Disease | MPTP | 21.65723 | 99 |
| Parkinson's Disease | Neurotensin | 15.321875 | 78 |
| Parkinson's Disease | Potassium fluoride | 14.5241758 | 88 |
| Parkinson's Disease | Prodipine | 17.4640775 | 99 |
| Parkinson's Disease | Pseudocumene | 15.024285 | 77 |
| Parkinson's Disease | Ropinirole | 16.273715 | 99 |
| Parkinson's Disease | Sulfur | 16.033 | 88 |
| Parkinson's Disease | Taurine (L) | 15.643565 | 78 |
| Parkinson's Disease | Threonine (L) | 14.89005 | 77 |
| Parkinson's Disease | Vitamin E Nicotinate | 16.74408625 | 77 |
| Highest Possible Value for Parkinson's Disease Profile | | | 2379 |

FIG. 9

DETECTION OF CONDITIONS FROM SOUND

CROSS REFERENCE TO RELATED APPLICATIONS

This application is a continuation of, and claims priority to, co-pending U.S. patent application entitled "DETECTION OF CONDITIONS FROM SOUND" filed under Ser. No. 12/339,445 on Dec. 19, 2008, which claims priority to U.S. Provisional Patent Application entitled "DETECTION OF CONDITIONS FROM SOUND" filed under Ser. No. 61/015,535 on Dec. 20, 2007, both of which are incorporated herein by reference in their entirety.

BACKGROUND

The diagnosis of physiological conditions is currently facilitated through invasive, time consuming, and expensive procedures. These procedures utilize machinery and chemical-based methods, and are usually narrowly targeted. These procedures do not provide a comprehensive evaluation of the human body, so it is possible that physiological conditions may go undiagnosed, resulting in a poorer quality of life.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 5 is a truth table diagram that provides one example of the identification of substantial zero slopes in the frequencies of the sound print as set forth in the graph of FIGS. 2 and 4 according to an embodiment of the present invention;

FIG. 6 is a truth table diagram that provides one example of identification of frequency ranges as set forth in the graph of FIGS. 2 and 4 according to an embodiment of the present invention;

FIG. 8 is a table that provides one example of identifying the substances falling within frequency ranges such as those illustrated in FIG. 6 according to an embodiment of the present invention;

FIG. 9 is a table that provides one example of a physiological profile employed in the sound diagnosis system of FIG. 1 according to an embodiment of the present invention;

DETAILED DESCRIPTION

Figure 1:
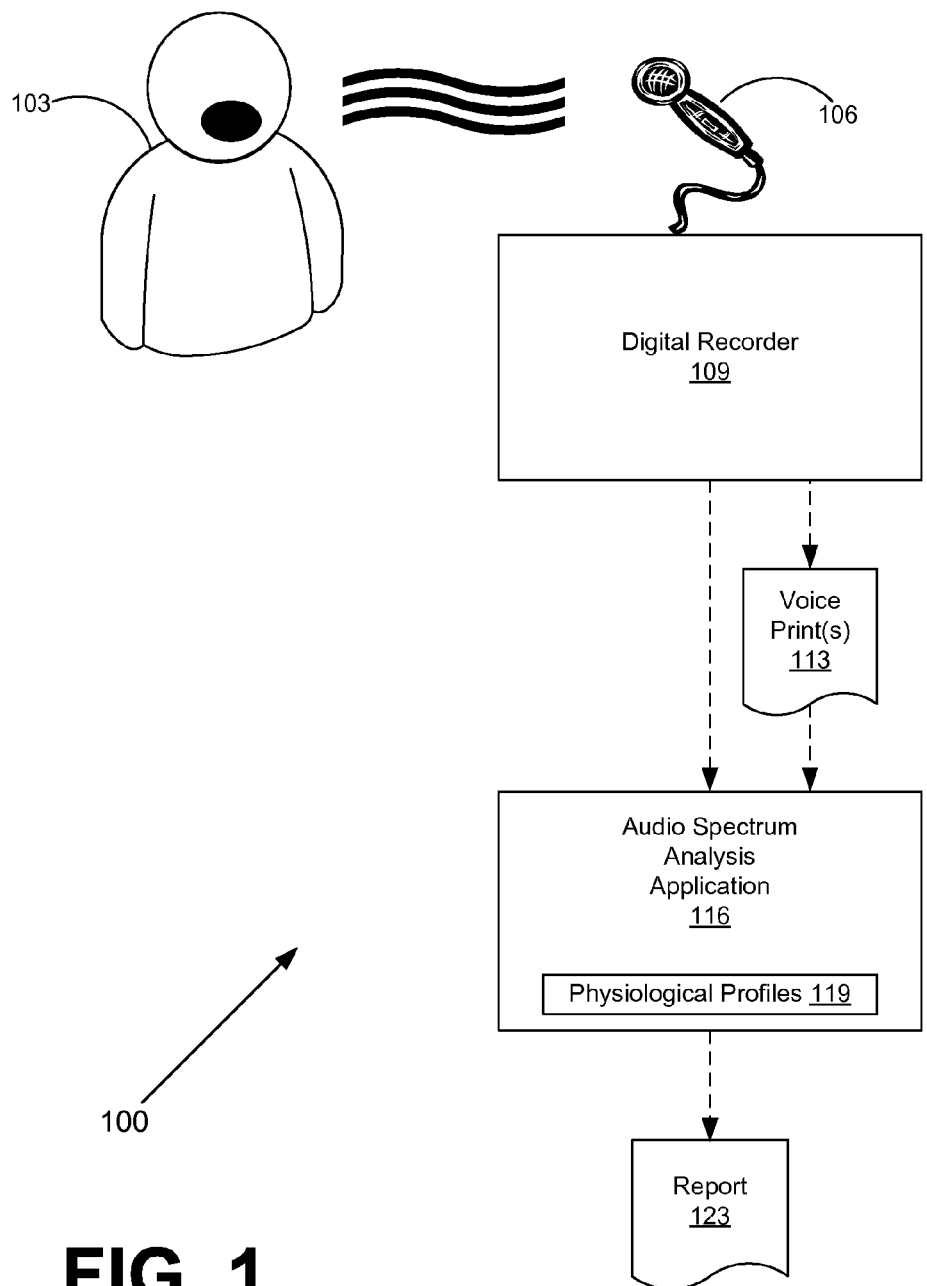
FIG. 1 is a block diagram that provides one example of a sound diagnosis system according to an embodiment of the present invention.

With reference to FIG. 1, shown is a sound diagnosis environment 300 according to an embodiment of the present invention. The sound diagnosis system 100 includes a microphone 106 coupled to a recorder 109. The recorder 109 is used to create a recording when a subject 103 speaks into the microphone 106, and save the recording as a sound print 113. Multiple sound print(s) 113 may be created by the recorder 109. These sound print(s) are then processed by the Audio Spectrum Analysis Application 116. The Audio Spectrum Analysis Application identifies signatures at various frequency ranges in the sound print(s) 113 as will be described. These frequencies are cross-referenced against stored physiological profiles 119, in order to generate a report 123 that may be used, for example, to provide a medical diagnosis for the subject 103.

In the sound diagnosis system 100, the subject 103 of the sound diagnosis may be, for example, an individual, though this may also apply to other sound generating entities or systems that a signal can be sent through for analytical purposes. The subject 103 may, for example, speak into a microphone 106 that is coupled to a recorder 109 for thirty seconds to one minute, or any other appropriate time period.

The subject 103 may speak into the microphone multiple times, wherein each time, the subject 103 is asked to speak about various topics. In one embodiment, the subject 103 may be asked to speak into the microphone 106 three different times. The topics are chosen such that they capture as much frequency information as possible from the subject 103. These topics may cause the pitch of the person's 103 voice to change as they are speaking. The topics that the person speaks about may include, for example, something that causes the subject 103 to feel stress, to feel happiness, to be reflective, or other topics.

Each sound print 113 generated is saved as a separate file. According to various embodiments, the sound print(s) 113 are recorded at a sufficient frequency range in order to have enough frequency information to detect physiological conditions. In one embodiment, a sufficient frequency range, such as, for example, 0 Hz-27 kHz is acceptable although higher or lower frequency ranges may be specified. The sound print(s) 113 may be recorded in multiple formats, including but not limited to .wav audio formats, .au audio formats, or any other acceptable format.

Once the sound print(s) 113 have been recorded using the recorder 109, they are analyzed using the audio spectrum analysis application 116. The audio spectrum analysis application 116 identifies signatures in the frequency spectrums of each of the sound print(s) 113. The signatures may be, for example, patterns, peaks, nulls, amplitude drifts, amplitude variations, or other signatures in the frequencies of each of the sound print(s) 113. These signatures may also be for example, substantial zero slopes, as will be described. These signatures may be, for example, indicative of a physical condition or ailment in the subject 103 as will be described.

The signatures may be associated with, for example, an imbalance existing within the human body. Such an imbalance may comprise for example, an abnormally high concentration or excessive amount of a substance. Alternatively, the imbalance may be an unusual lack of a substance. Various frequencies are associated with such substances. Once the audio spectrum analysis application 116 identifies signatures associated with substances in a given sound print, the frequencies of these substances may, for example, be cross-referenced against the frequencies of the substances associated with stored physiological profiles 119.

A physiological profile 119 is a record of the imbalances associated with persons who have a known medical condition such as Parkinson's disease or Alzheimer's disease. The medical condition can be any medical condition including diseases, deficiencies, and ailments. These medical conditions may be associated with a plurality of imbalances associated with substances in the human body or other anomalies as will be discussed. A physiological profile 119 thus may contain, for example, a list of substances, or frequencies subject to an imbalance that are found in a given subject with a known condition. In one embodiment, the list of substances or frequencies associated with a physiological profile may be a subset of the total substances or frequencies associated with a subject. The subset may comprise the primary substances associated with a medical or other condition.

By cross-referencing the frequencies of the substances identified in the sound print 113 with the frequencies of the substances associated with the stored physiological profiles 119, a list of the physiological profiles 119 that are most relevant to the subject 103 of the sound print may be generated. When cross-referencing, the frequencies of the substances identified in the sound print 113 are matched to the frequencies of the substances associated with the physiological profiles 119. If a significant number of the substances associated with a physiological profile 119 are matched with substances identified in a given sound print 113, then the medical condition associated with the physiological profile is potentially applicable to the subject 103 who produced the sound print 113. It may be considered significant if a predefined percentage of the imbalances associated with substances of a profile are matched to the substances found in a given sound print 113. For example, that percentage may be 70% or more.

Once the audio spectrum analysis application 116 identifies the physiological profiles 119 most relevant to the subject of the sound print 113, these physiological profiles may be prioritized based on the percentage of matches between imbalances associated with the sound print 113 and imbalances associated with the substances of a physiological profile 119. The audio spectrum analysis application 116 generates a report 123 detailing the potential matches and therefore, the potential medical conditions that may be associated with the sound print. The report 123 may contain, for example, those physiological profiles 119 that are most relevant to the person, and may be used, for example, to diagnose whether the subject 103 has certain medical conditions.

Figure 2:
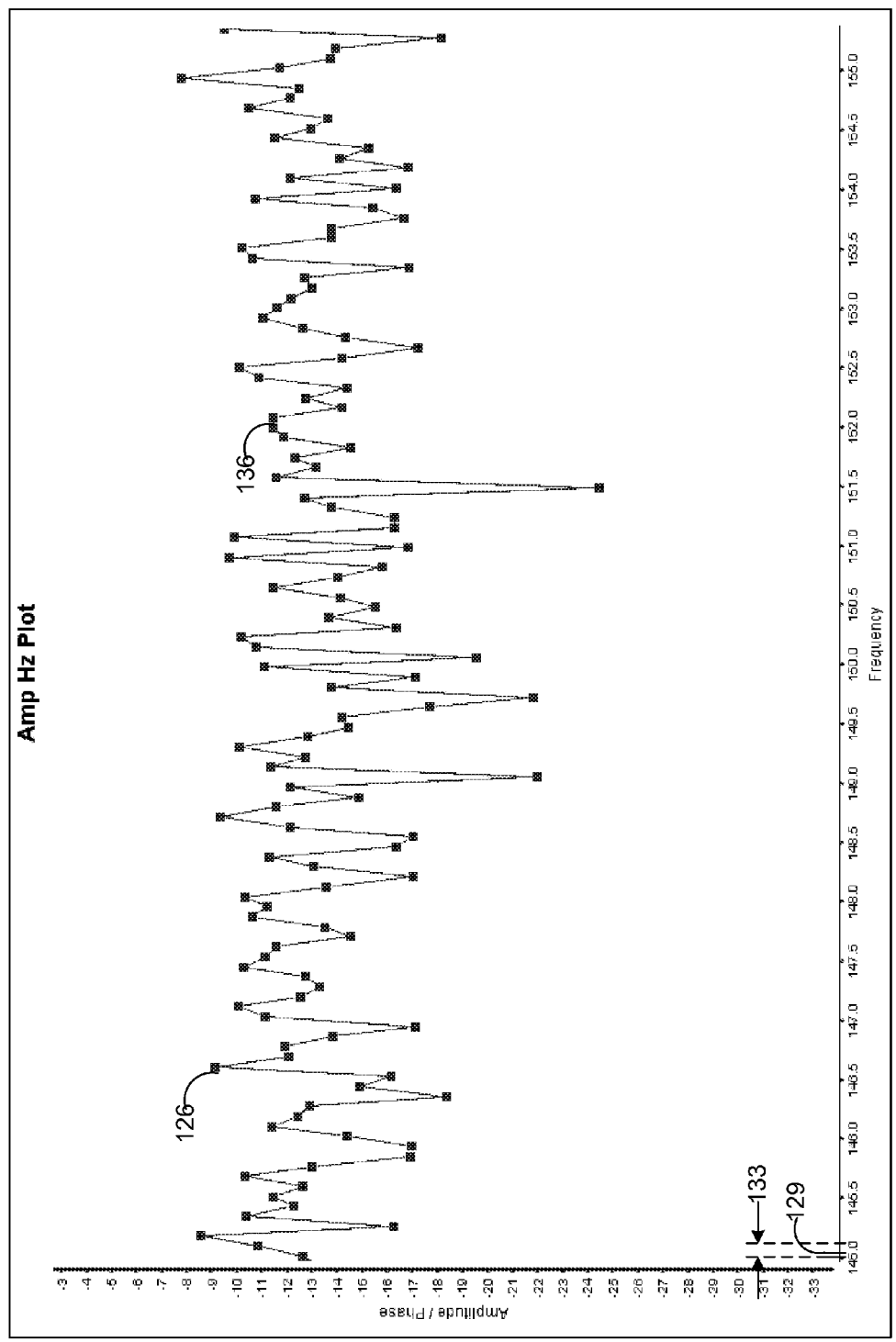
FIG. 2 is a graph that provides one example of a frequency plot of a sound print that is generated from a Frequency Transform implemented during the audio spectrum analysis in the sound diagnosis system of FIG. 1 according to an embodiment of the present invention.

With reference to FIG. 2, shown is an example of a portion of a frequency plot of a sound print 113 (FIG. 1) after the sound print 113 has been processed through a frequency spectral conversion, such as, for example, a Frequency Transform, by the audio spectrum analysis application 116 (FIG. 1). Each measurement point 126 on the plot represents a measurement that was taken at a specific frequency interval 129. In one embodiment, the resolution is such that the frequency intervals 129 are, for example, every 0.04 Hz such that there is a measurement point 126 every 0.04 Hz. A frequency band 133 may contain, for example, multiple frequency measurement points. For example, where the frequency band 133 is specified as 0.33 Hz and a frequency measurement point 126 has been generated every 0.04 Hz, a frequency band 133 would contain eight frequency measurement points 126.

The audio spectrum analysis application 116 identifies signatures 136 in the sound print 113 by evaluating the sound print 113 at each measurement point 126. These signatures may be, for example, peaks, nulls or patterns in the frequency plot. In one embodiment, these signatures are, for example, substantial zero slopes found in the frequency plot of the sound print 113. A substantial zero slope 136 occurs where the maximum amplitude shift is less than a predefined threshold over a given frequency band 133. Stated another way, the maximum slope between any two of the points of measurement 126 of the frequency band 133 is less than a predefined maximum slope threshold. In one embodiment, the maximum amplitude frequency slope is substantially equal to zero if the change in amplitude is no greater than 0.15 dB between any two measurement points 126 for a given frequency band 133 of 0.33 Hz., where amplitude shift is measured at every adjacent pair of measurement points 126. Alternatively, signatures may be defined in some other manner.

Figure 3:
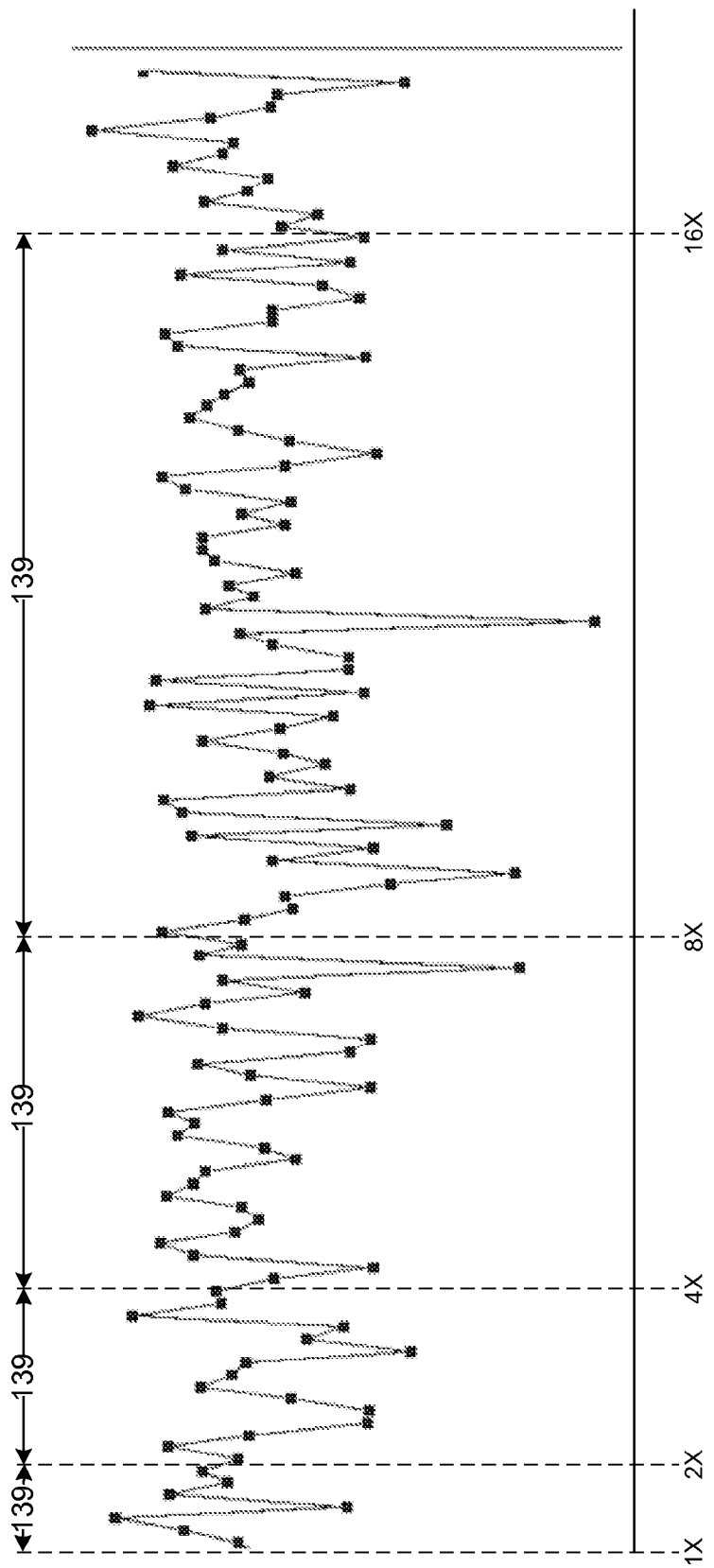
FIG. 3 is a diagram that provides one example of the multiple octaves of a sound print generated by the sound diagnosis system according to an embodiment of the present invention.

Next, with reference to FIG. 3, shown is a diagram denoting the multiple octaves 139 associated with the same sound print 113 for a portion of a frequency plot of the sound print 113 (FIG. 1) over a specific frequency interval. It has been found that a signature at a predefined frequency may be repeated at the harmonics of such a frequency. A given frequency spectrum of a sound print may be split up into octaves. Thus, if a given signature is found at a predefined frequency, the octaves above that frequency may be examined to see if the same signature appears at the multiples of such a frequency. Therefore, multiple octaves may be examined for a given sound print 113 in order to identify a greater number of signatures 136 (FIG. 2) in a sound print 113. The number of octaves at which a signature appears will correspond to the severity of the imbalance experienced in the subject 103 (FIG. 1). That is to say, the more severe an imbalance, then the signature will appear at a greater number of octaves of the base frequency associated with the imbalance.

For illustrative purposes, FIG. 3 shows four octaves 139, however any number of octaves may be examined within the frequency spectrum. In one embodiment, six octaves may be examined in order to achieve advantageous results for identifying signatures 136 in a sound print 113. In FIG. 3, each octave 139 has a frequency range that is twice that of the preceding octave 139. For example, the frequency range of Octave 2 is twice the frequency range of Octave 1, where Octave 1 is the base frequency at which a given signature may have been detected. For illustrative purposes, FIG. 3 demonstrates how the Octaves may be viewed relative to one another for a given frequency interval 129 for the purposes of plotting the octaves 139, as will be described.

Figure 4:
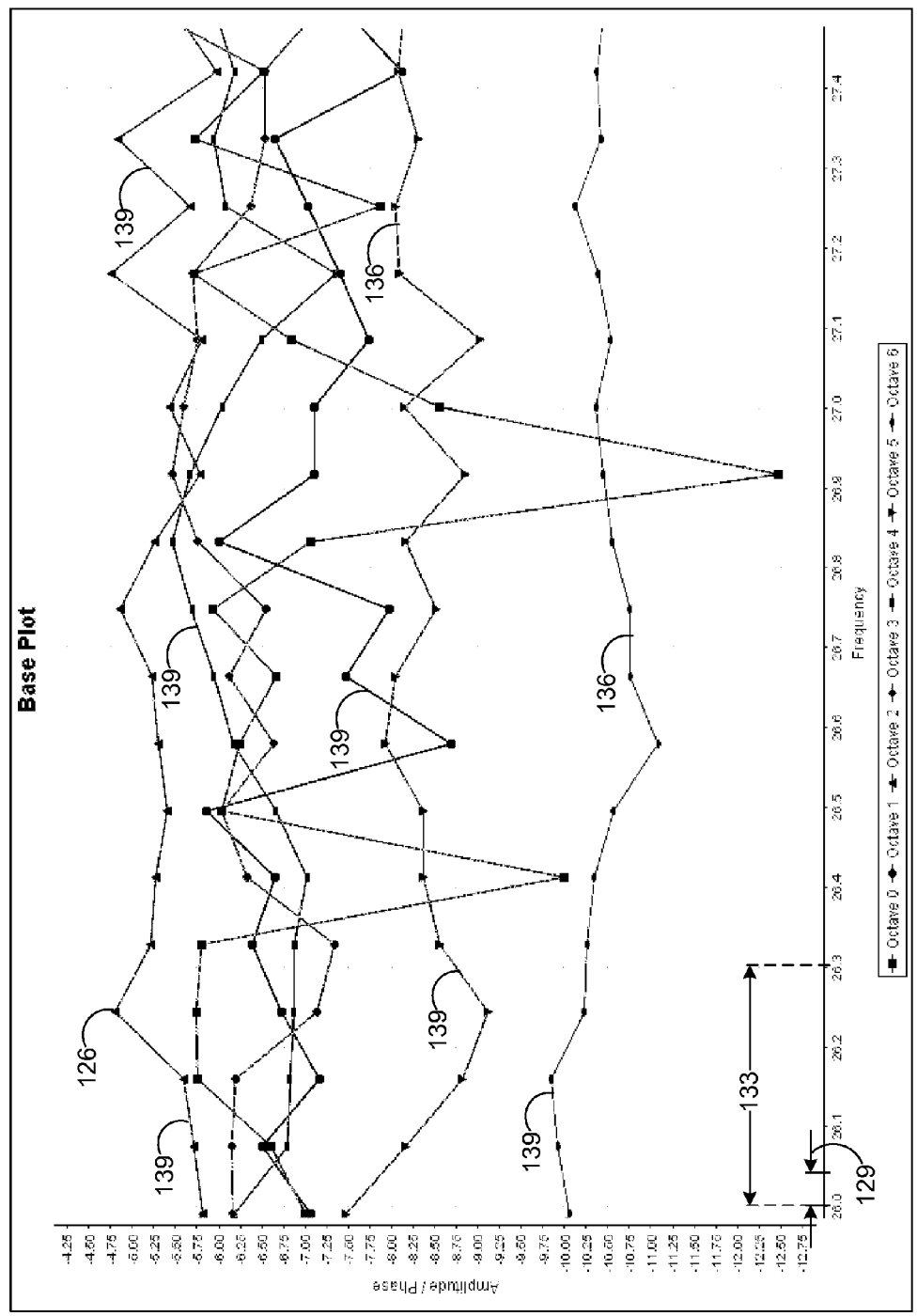
FIG. 4 is a graph that provides one example of a frequency plot of octaves of a sound print that is generated from the Fast Fourier implemented during the audio spectrum analysis employed in the sound diagnosis system of FIG. 1 according to an embodiment of the present invention.

With reference to FIG. 4, shown is a portion of a frequency plot of multiple octaves 139 of a sound print 113 (FIG. 1) after the sound print has been processed through a frequency spectral conversion, for example, a Fast Fourier Transform, by the audio spectrum analysis application 116 (FIG. 1). For illustrative purposes, this plot shows six octaves 139. The portions of the frequency plot that include the octaves 139 as described in FIG. 3 have been transposed over one another such that the octaves are in alignment.

The slope between two measurement points 126 is analyzed for each octave 136 at defined frequency intervals 129 associated with the base frequency range. In one embodiment, the frequency interval 129 is, for example, 0.04 Hz. The audio spectrum analysis application 116 may, for example, identify signatures 136 in the sound print 113 by evaluating each octave of the sound print 113 at the slope between each of the measurement points 126. In one embodiment, these signatures may be, for example, substantial zero slopes found in the frequency plot of the sound print 113. A substantial zero slope 136 occurs where the maximum amplitude variation or maximum slope between each of the measurement points 126 falling within a given frequency band 133 falls below the predefined threshold as described above. In one embodiment, the maximum amplitude shift is approximately 0.15 dB over a total frequency band 133 of 0.33 Hz where the amplitude shift is measured every 0.04 Hz, although other thresholds may be specified. Note that if the maximum variation threshold or corresponding slope threshold is set too high, then signatures may be misidentified.

Once the audio spectrum analysis application 116 has identified all signatures 136 at each frequency band 133 for each octave 139, this information may be organized in such a manner as to ascertain whether the individual signatures are significant such that they are indicative of some imbalance or anomaly in the subject 103 (FIG. 1). This organization may, for example, increase the accuracy of identifying meaningful imbalances associated with substances in the subject. In one embodiment, a truth table may be used to correlate if a signature 136 was identified at the harmonics associated with a given base frequency band 133 as determined from the octaves 139.

Next, shown in FIG. 5 is a truth table that may be used to ascertain the appearance of signatures 136 (FIG. 4) at the base frequency within a sound print 113 (FIG. 1) based upon the operative measurement points 126, in a given frequency band 133, for each octave 139 that includes harmonics of the base frequencies. The truth table may combine all of the octave 139 information for each sound print 113 that was taken from a subject 103 (FIG. 1). Each field 136 in the truth table may contain, for example, a TRUE (or "1") or a FALSE (or "0") indicating if a signature 136 has been identified in an octave 136 at a given frequency band 133.

In one embodiment, if a signature, such as a substantial zero slope, has been identified by the audio spectrum analysis application 116 (FIG. 1) for a given frequency band 133, then a TRUE is entered in the corresponding field 136 in the truth table. For example, the field 136 would contain a TRUE (or '1') if, for a frequency band 133 of 0.33 Hz, the amplitude shift at each 0.04 Hz measurement point 126 was less than 0.15 dB. Alternatively, some other anomaly may be detected in a given frequency band 133.

The truth table may be formatted such that all fields contain either a TRUE or a FALSE. The total number of signatures 136 that appear at a given frequency band 133 may be totaled. In one embodiment, the total number of signatures that appear at a given frequency band 133 is known as the total number of hits 143. The total number of hits 143 at a given frequency band 133 may be used to determine the significance of that frequency band 133. For example, the higher the total number of hits 143, the more likely it is that it is indicative of a physical condition or ailment in the subject such as person 103.

Next, FIG. 6 represents a truth table where the total number of hits 143 at each frequency band 133 is compared against a threshold 149. This comparison is used to determine whether or not the number of signatures 136 (FIG. 4) identified at the frequency band 133 are sufficient to indicate a physical condition or ailment in the subject 103 (FIG. 1). In one embodiment, for each frequency band 133, the total number of hits represents the number of signatures, such as substantial zero slopes, that were identified by the audio spectrum analysis application 116 (FIG. 1) at that given frequency band 133. If the total number of hits 143 is, for example, greater than the threshold 149 then a TRUE is entered into the result 153 field in the truth table. The threshold 149, shown for illustrative purposes here as '5', represents at least the number of signatures that need to be identified at a frequency band 133, and its corresponding resonant frequencies, for that band 133 to have significance. In one embodiment, the threshold may be half the total number of octaves 139 plus one or some other threshold.

The result 153 of the comparison is entered into the truth table, and may, for example, be a "TRUE" or a "FALSE". The results 153 are used to identify frequency ranges 146 that comprise one or more frequency bands 133 as shown. When the result 153 is "TRUE", then that frequency band 133 translates to a frequency range 146. When the result 153 is "TRUE" for two or more adjacent frequency bands 133, then the frequency range 146 will comprise all of the adjacent frequency bands 133 together. In one embodiment, if a frequency band 133 has total hits 143 that are greater than the threshold 149, then frequency band 133 is added to a frequency range 146. For example, the smallest frequency of a frequency band 133 may be a discrete beginning point of a frequency range 146, or alternatively the largest frequency of a frequency band 133 may be the ending point of a frequency range. The frequency ranges 146 may comprise, for example, all frequencies within the frequency bands 133 that make up the frequency range 143.

For example, if "Freq. Band 8" represents a frequency band 133 of 33.0 Hz-33.12 Hz and "Freq. Band 9" represents a frequency band 133 of 33.13 Hz-33.24 Hz, the corresponding frequency range 146 would contain all frequencies between 33.0 Hz-33.24 Hz. The frequency band 133 represented by "Freq. Band 10", for example 33.25 Hz-33.36 Hz, would not be included in the prior frequency range 146 because the total number of hits 143 at frequency band 133 "Freq. Band 10" does not exceed the threshold 149. These thresholds may be varied for optimum results.

In the preceding example, the next subsequent frequency range 146 would begin at the lowest end frequency of the next frequency band 133 that had a total number of hits 143 exceeding the threshold 149. Each frequency range 146 may have a different width, or magnitude. Once all of the frequency ranges 146 have been identified, they may be prioritized and ranked. In one embodiment of the invention, the frequency ranges 146 may be prioritized by the width. For example, the frequency ranges 146 with greater width are given a higher priority than the frequency ranges 146 with small magnitudes. In one embodiment, once the frequency ranges 146 have been prioritized, they may be ranked by the number of frequency ranges 146 identified. For example, if 36 frequency ranges 146 have been identified, then the frequency range with the greatest width, or the highest priority, would be ranked 1 and so forth. Alternatively, another type of ranking might be considered.

Figure 7:
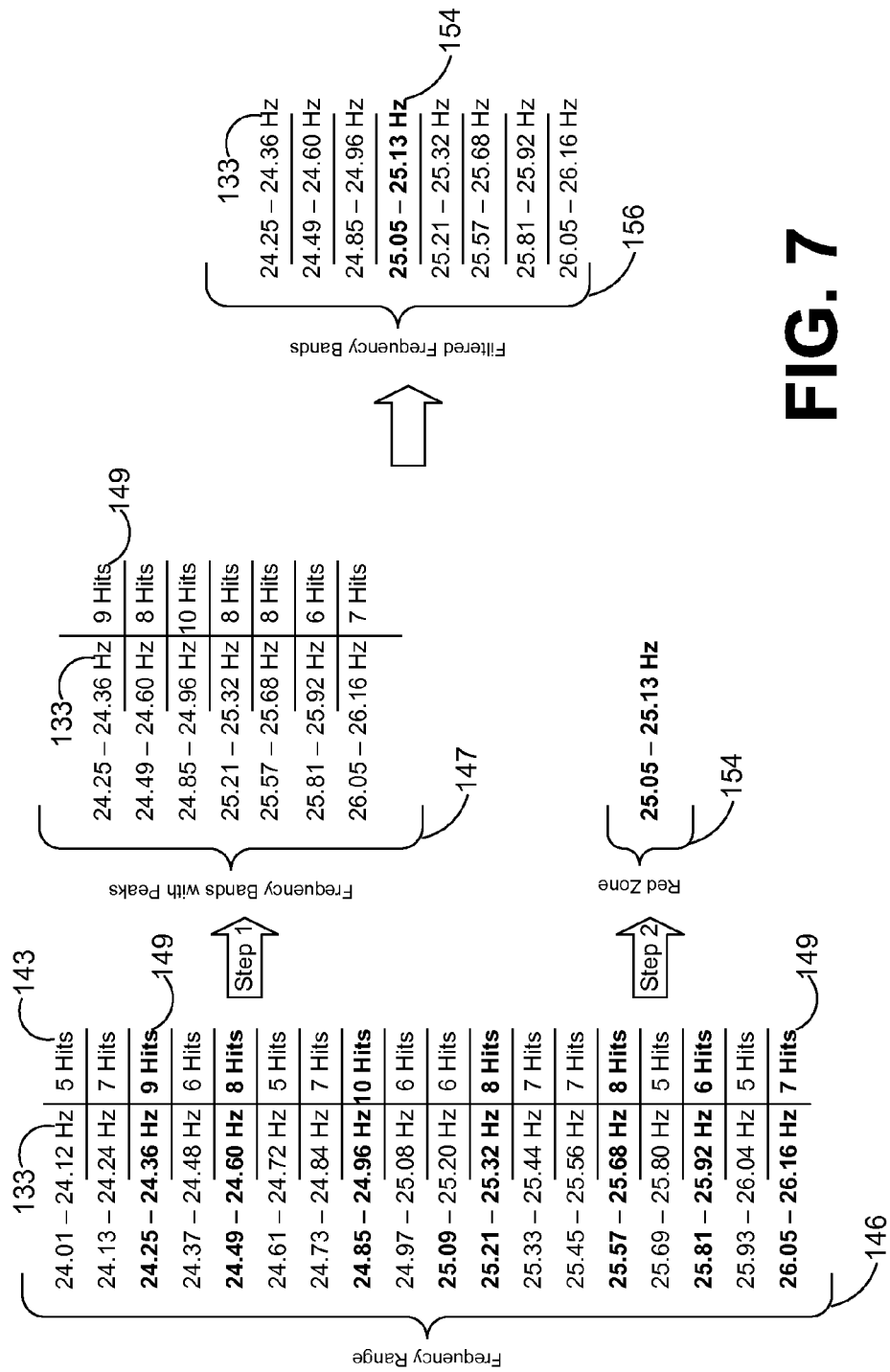
FIG. 7 is a diagram that provides one example of identifying the filtered frequency bands from the frequency ranges as set forth in FIG. 6 according to an embodiment of the present invention.

Next, FIG. 7 represents a second prioritization that may be employed for the list of frequency ranges 146. This prioritization may be used, for example, after the frequency ranges have been prioritized according to width as described above. The purpose of this prioritization is to identify "peaks" 149 and "red zones" 154 within the frequency ranges 146, as will be explained. This prioritization may, for example, reduce the probability that the data within the frequency ranges 146 is coincidental.

In the first step of this prioritization, the peaks 149 within the frequency range 146 are identified. In one embodiment, a peak 149 occurs where the total number of hits 143 are the greatest within a sequence of frequency bands 133 within the frequency range 146. For example, if the number of hits 143 at the 24.010-24.120 Hz frequency band 133 is 5, the number of hits 143 at the 24.130-24.240 Hz frequency band 133 is 7, the number of hits at the 24.250-24.360 Hz frequency band 133 is 9, and the number of hits at the 24.370-24.480 Hz frequency band is 6, then there is a peak 149 at the 24.250-24.360 Hz frequency band. The frequency bands 133 where the peaks 149 existed are filtered from the other frequency bands 133 within the frequency range 146 in order to create a list of frequency bands with peaks 147.

In the second step of this prioritization, the red zone 154 within the frequency range 146 is identified. In one embodiment, the red zone 154 contains all of the frequencies within a given distance from the midpoint, or center, of the frequency range 146. For example, all frequencies within 0.04 Hz of the midpoint 148 of the frequency range make up the red zone 154. As illustrated in FIG. 7, if the frequency range 146 is 24.010-26.160 Hz then the midpoint is 25.085 Hz. The red zone 154 is 25.050-25.130 Hz. Alternatively, other ranges may be used for the red zone.

In one embodiment, the frequency range 146 may be reduced to a filtered list 156 that contains only those frequency bands with peaks 147 and the frequencies within the red zone 154. Once the filtered frequency bands 156 have been ascertained by the audio spectrum analysis application 116, they may be used, for example, to identify imbalances associated with substances within the subject 103. It has been discovered that the midpoint of a red zone 154 may, for example, be indicative of the substance associated with an imbalance in the subject 103 (FIG. 1), whereas the frequencies in the red zone 154 surrounding the mid point may indicate the cause of the imbalance.

Next, FIG. 8 represents a table containing a list of substances 159 with their corresponding frequencies 163, profiles 166, and categories 169. For example, to determine the frequency 163 for a given substance, one may consult Meyer William L., Neff, Georgia, Ph.D., Garfield-O'Brien, and Lauren, R. N., *A Summary of Sound Therapy and Vibrational Healing Concepts Book* 1, published on the Internet at http://bioadaptech.com/concepts1.pdf, December 2003, which is incorporated herein by reference. The frequencies 163 of these substances 159 are compared against those frequencies falling within the list of filtered frequency bands 156. In one embodiment, if a frequency 163 of a substance 159 falls within a list of filtered frequency bands 156, then it may indicate that an imbalance associated with that substance 159 exists within the subject 103 (FIG. 1).

In one embodiment, the substances 159, that appear in the table may include, but are not limited to, enzymes, chemicals, parasites, and proteins. Each substance has a corresponding resonant or other associated frequency. The substances 159 may be ranked according to the priority and ranking of the frequency ranges 146 from which the lists filtered frequency bands 156, within which the substances 159 fall, were extracted. In one embodiment, once all of the substances 159 falling within the lists of filtered frequency bands 156 have been identified and ranked, then the list of substances 159 may be cut off at a pre-defined number. For example, the list of substances may be shortened to contain only the top 2000 substances or other number. This reduces the number of substances to be analyzed and considered.

According to an embodiment of the present invention, the substances 159 with frequencies 163 falling within the lists of filtered frequency bands 156 may be associated with an imbalance in the subject 103. These imbalances may be indicative of a physical condition or ailment in the subject 103. Thus, the frequencies 163 associated with the identified substances 159 may, for example, be cross-referenced against the frequencies of substances associated with known physiological profiles 119, as will be described. Where substantial matches occurred, there is a probability that the subject 103 may have the condition associated with the profile as will be described.

Next, FIG. 9 represents a table containing an example of a known physiological profile 119 with corresponding substances 173, the resonant frequencies 176 of the respective substance 173, and the percentage of recurrence of that substance within the data set used to generate the profile 119. The substances 173 within the physiological profiles may be matched with the list of identified substances 159 (FIG. 8) in order to identify physiological profiles 119 that are potentially applicable to the subject 103. Stated in another way, in one embodiment, the frequencies 163 of the substances 159 (FIG. 8) potentially associated with an imbalance are identified in the subject 103 (FIG. 1) and are cross-referenced with the frequencies 176 of the substances 173 associated with physiological profiles 119.

Each physiological profile 119 may be, for example, associated with one or more physiological or medical conditions such as Adrenal Stress, Allergies, Alzheimer's disease, or anyone of many other conditions. Some of the profiles are associated with categories such as, for example, toxic profiles, element profiles, vertebra profiles, and microorganism profiles. In an embodiment of the invention, in the table of physiological profiles 119, the substances 173 associated with each physiological profile 119 may be the substances most consistently found in a population of people suffering from the respective condition listed in the physiological profile 119.

Each of the substances 173 within a profile may have a weight 179 that represents, for example, their importance and recurrence within the profile 119. For example, the substance 173 calcium sulfate may have an importance and recurrence weight of 88, out of a possible 100, in people suffering from Parkinson's Disease. The profiles 119 may be generated, for example, though empirical research by taking sample sound prints 113 of subjects who are known to have the condition and by compiling information found in the public domain. As discussed above, the frequency 176 of each substance 173 is determined as disclosed in the Meyer reference listed above. The weights 179 may be totaled for each profile 119 in order to determine the highest possible weight 180, or point value, for the respective profile.

Figure 10:
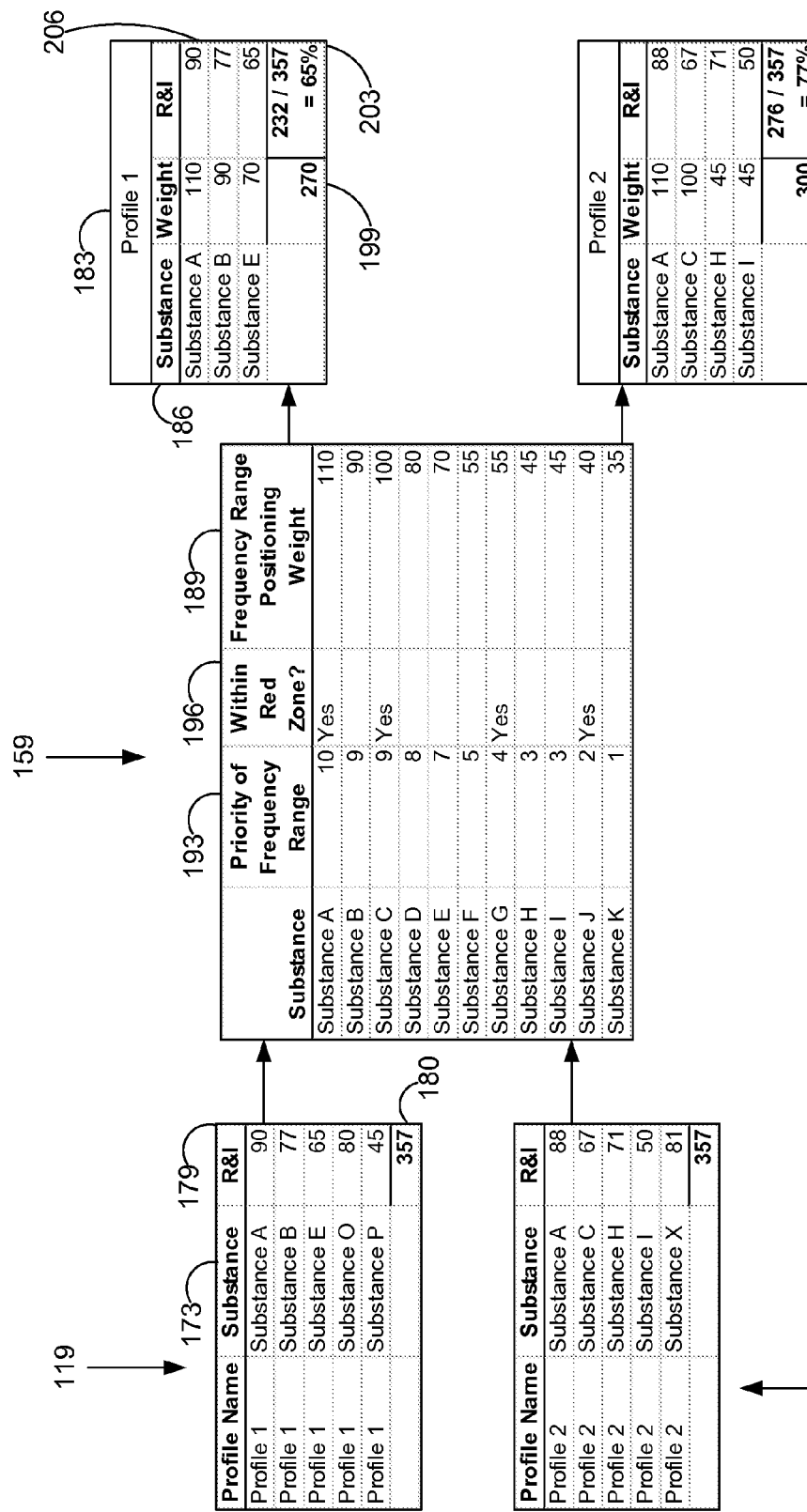
FIG. 10 is a diagram that illustrates the identification of profiles applicable to the subject of the sound diagnosis system of FIG. 1 according to an embodiment of the present invention.

Next, FIG. 10 represents the identification of profiles applicable to the subject 103 (FIG. 1) who is the subject of the analysis. In an embodiment of the invention, through a multi-step process, the profiles applicable to a subject 103 are weighted and given a designation of importance. For example, this designation might be Chronic, Major, or Minor, as will be discussed.

In one embodiment, the first step in identifying profiles applicable to a subject 103 is to cross-reference the substances 173 associated with a profile 119 against the list of substances 159 (FIG. 8) in order to generate a sub-report 183 for the user containing the matched substances 186 associated with the subject 103. In one embodiment, the frequencies 163 (FIG. 8) of the substances 159 identified in the subject 103 are cross-referenced with the frequencies 176 (FIG. 9) of the substances 173 associated with physiological profiles 119. If the frequencies are matched then the substance 186 is added to the sub-report 183 of the respective profile 119 for the subject 103. For example, if the frequency of Substance A 173, found in Profile 1 119 matched the frequency of Substance A 159, the Substance A 186 would be identified in the sub-report 183 for Profile 1.

Each substance 159 has an associated frequency range positioning weight 189. The weight 189 for each substance 159 may be calculated based upon the priority of the frequency range 193 within which the frequency 163 (FIG. 8) of the substance 159 falls. In one embodiment, a frequency range 146 will be weighted between 100 and 0 points based upon its priority, where the increment changes by 10 points until the halfway point is reached in the list of frequency ranges. Once the halfway point is reached in the list of frequency ranges, then the increment changed by 5 points. Alternatively, different increments may be used. The weight 189 of each substance may also be affected if the substance 159 falls within the red zone of the respective frequency range 196. In one embodiment, if the substance 159 falls within the red zone of the frequency range 196, an additional 10 points, or other number, is added to the weight 189. For example, Substance A falls within the frequency range 146 with the highest priority (100) and falls within the red zone of that frequency range 146. Consequently, substance A has a frequency range positioning weight 189 of 110 points.

Once the substances 186 have been identified for the sub-report 183 of the respective profile 119, a total frequency range positioning weight 199 may be calculated by totaling the frequency range positioning weight 189 for each substance 186. In one embodiment, the summation of the total frequency range positioning weight 199 of a profile with the profile substance weight percentage 203 may be used to assign a priority to the sub-report 183 such that a higher summation would correlate with a higher priority. The profile substance weight percentage 203 may be determined by totaling the recurrence and importance weights 206 for each substance within a sub-report 183 and dividing that total by the highest possible weight 180 for the profile 119 in the given sub-report 183. For example, the total recurrence and importance weight for Profile 1 sub-report 183 is 232, which is divided by 357, the highest possible weight 180 for Profile 1, in order to generate a profile substance weight percentage of 65%. Thus, Profile 1 may be 65% applicable to the subject 103 (FIG. 1).

In various embodiments, the profile substance percentage 203 of a sub-report 183 may be evaluated to determine whether the sub-report 183 should be dropped from the analysis by assigning either a positive or negative status to the sub-report 183 for a given profile. The positive or negative status may be assigned based upon a given percentage threshold for the profile substance percentage 203. For example, if the profile substance percentage is greater than or equal to 20% then the sub-report 183 for a given profile is assigned a positive status. Alternatively, if the profile substance percentage is less than 20% then the sub-report 183 for a given profile is assigned a negative status. In one embodiment, sub-reports 183 that have been assigned a negative status may be dropped from the final report 123 (FIG. 1).

Additionally, the profile substance percentage 203 of a sub-report 183 of a given profile may be used to determine a designation for the sub-report 183. This designation may be, for example, Chronic, Major, or Minor. In one embodiment, the designation is assigned based upon a given percentage threshold for the profile substance percentage 203. For example, if the profile substance percentage is greater than or equal to 80% then the sub-report 183 for a given profile will be designated as chronic.

The sub-reports 189 that identify profiles 119 potentially applicable to the subject 103 may be, for example, combined to generate an overall client profile for the subject 103. This overall client profile may be provided as a report 123. In one embodiment, the report 123 contains, for example, the sub-reports 189 of the profiles 119 that are most applicable to the subject 103. These profiles 119 may be prioritized in the overall client profile for the subject 103.

Figure 11:
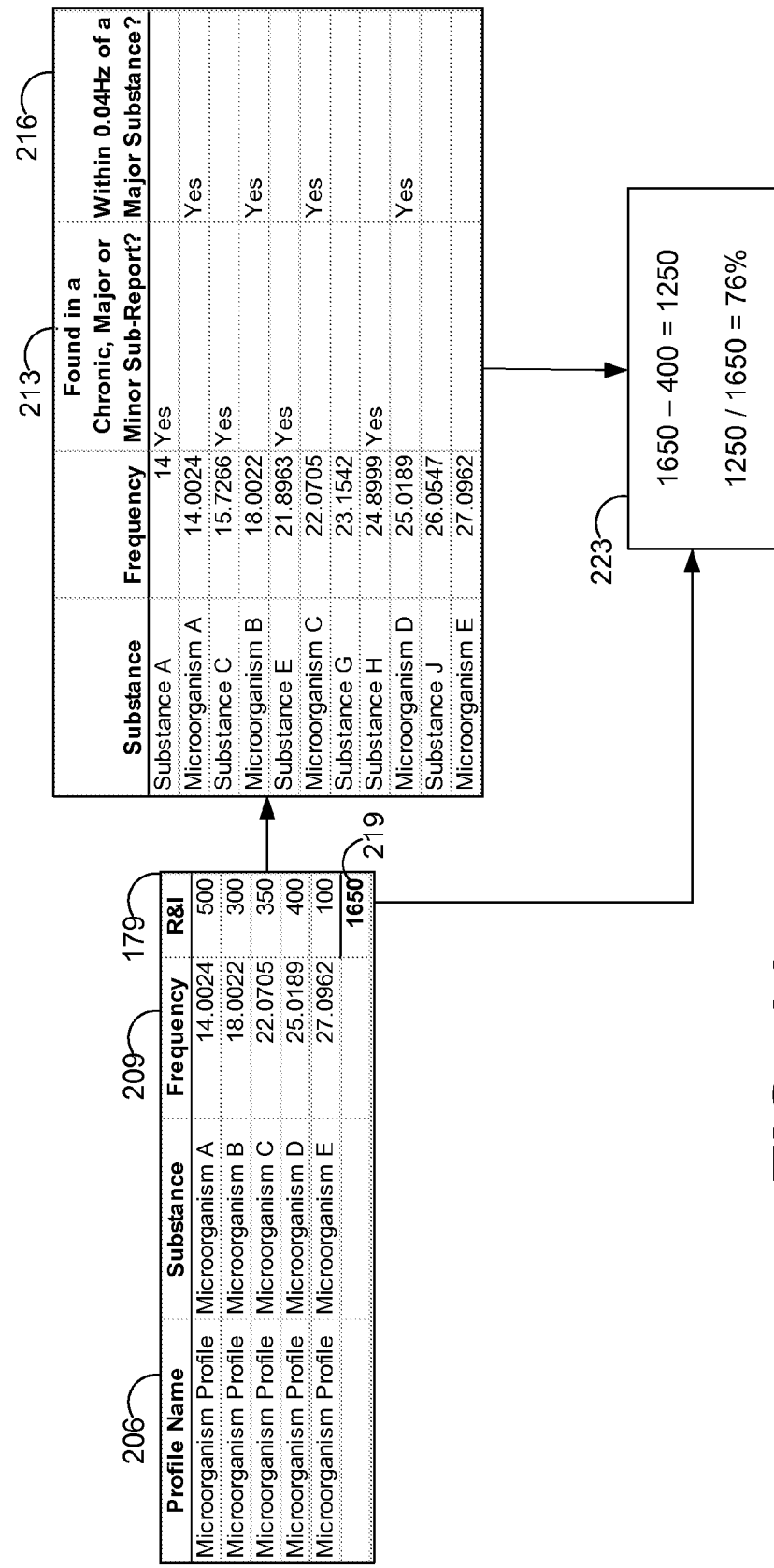
FIG. 11 is a diagram that illustrates an additional stage in the identification of profiles applicable to the subject of the sound diagnosis system of FIG. 1 according to an embodiment of the present invention.

Next, FIG. 11 represents an additional stage in the identification of profiles applicable to the subject 103 (FIG. 1) of the analysis. In various embodiments of the invention, an additional step in the generation of sub-reports 183 may occur through the analysis of profiles 119 that are categorized as microorganism profiles 206. A microorganism profile 206 may represent, for example, one species of a microorganism, such as Salmonella, and contain all of the resonant frequencies 209 associated with the respective microorganism.

In one embodiment, the proximity 216 of the frequencies 209 associated with the respective microorganism to the frequencies of major substances is analyzed, and the weight 219 of the microorganism profile 206 may be adjusted. A substance may be considered a major substance 213 if, for example, it appears in a sub-report 183 (FIG. 10) that has been designated as either Chronic, Major, or Minor as described above. If the proximity 216 of the frequency 209 associated with a microorganism is, for example, within 0.04 Hz of the frequency of a major substance 216 then the frequency 209 is considered within the necessary proximity 216 of the frequency of a major substance 216 such that the weight 219 of the microorganism profile 206 needs to be adjusted. The adjustment is made by deducting 100 points from the total weight 219 of the microorganism profile. Once a deduction has been made for each frequency 209 within the determined proximity 216 of the frequency of a major substance 213, then the total weight 219 is divided by the highest possible weight for the microorganism profile 206, as described above in relation to FIG. 9, in order to determine the percentage of applicability 223 to the subject 103 (FIG. 1).

Figure 12:
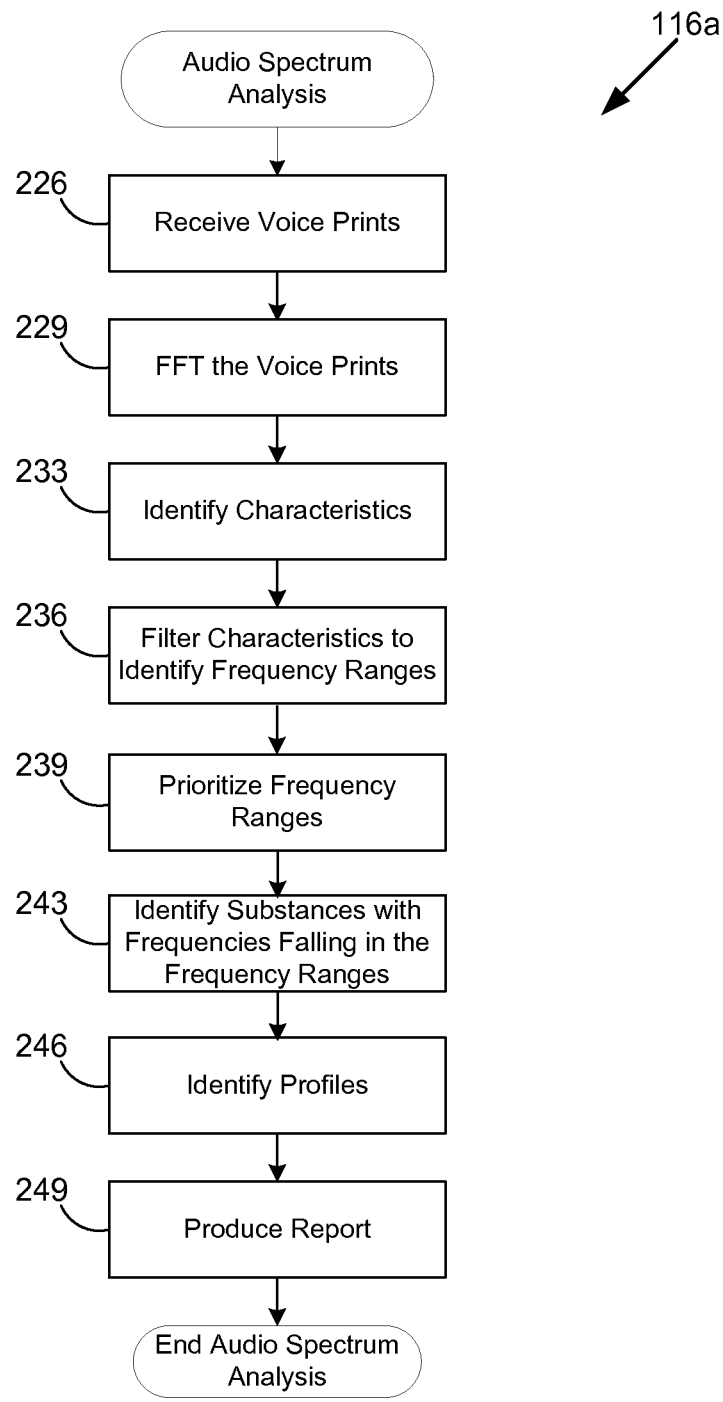
FIG. 12 is a flow chart that provides one example of an audio spectrum analysis that is employed in the sound diagnosis system of FIG. 1 according to an embodiment of the present invention.

Referring next to FIG. 12, shown is a flow chart that provides one example of the operation of the voice diagnosis system (FIG. 1) according to an embodiment of the present invention. Alternatively, the flow chart of FIG. 12 may be viewed as depicting steps of an example of a method implemented in the audio spectrum analysis application 116 to generate a client profile report 123 (FIG. 1). The functionality of vocal diagnosis system as depicted by the example flow chart of FIG. 12 may be implemented, for example, in an object-oriented design or in some other programming architecture. Assuming the functionality is implemented in an object oriented design, then each block represents functionality that may be implemented in one or more methods that are encapsulated in one or more objects. The vocal diagnosis system may be implemented using any one of a number of programming languages such as, for example, C, C++, JAVA, SQL, ASP, or other programming languages.

The flow chart provides for the analysis of sound print(s) 113 by the audio spectrum analysis application 116. The flow chart also provides for the generation a report 123 containing the sub-reports 189 (FIG. 10) and microorganism profiles 206 (FIG. 11) that are most potentially applicable to the subject 103 (FIG. 1).

Beginning with box 226, the audio spectrum analysis logic 116a receives the sound print(s) 113. In one embodiment, the sound print(s) 113 may be received from a client machine, as will be discussed. The sound print(s) 113 may be, for example, stored in the sound print(s) data store, as will be discussed. Thereafter, the audio spectrum analysis logic 116a proceeds to box 229.

Next, in box 229, the audio spectrum analysis logic 116a processes the sound print(s) 113 with a Frequency Transform to generate a frequency spectrum for the sound print(s) 113. By performing the Frequency Transform, the sound print(s) 113 can be analyzed in the frequency domain, as shown in FIGS. 2 and 4. Thereafter, the audio spectrum analysis logic 116a proceeds to box 209.

In box 233, the audio spectrum analysis logic 116a identifies signatures 136 in the sound print(s) 113. These signatures 136 may include, for example, substantial zero slopes 136 (FIG. 2). A substantial zero slope 136 occurs where the maximum amplitude variation between two of the points of measurement 126 (FIG. 2) falls below a predefined threshold as described above. Thereafter, the audio spectrum analysis logic 116a proceeds to box 213.

Next, in box 236, the audio spectrum analysis logic 116a filters the signatures 136. The signatures 136 may be filtered, for example, by determining which signatures occur at several octaves of a base frequency examined in the sound print (FIG. 5), as described above. If a signature is prominent at a frequency band 133, it is likely that the frequency band 133 is significant for determining the existence of imbalances associated with substances 153 in the subject 103. In one embodiment, the signature 136 is prominent at a frequency band 133 if the signature 136 is identified in multiple octaves 136. For example, the signatures 136 may be filtered in order to identify frequency ranges 143 (FIG. 6). A frequency range 143 is a magnitude of frequencies where signatures 136 exist in the sound print(s) 113. Thereafter, the audio spectrum analysis logic 116a proceeds to box 239.

In box 239, the audio spectrum analysis logic 116a prioritizes the frequency ranges 143. For example, frequency ranges 143 may be prioritized based upon the number of hits for each frequency range 143. In one embodiment, the greater the magnitude of the frequency range, the greater the priority it is given. Thereafter, the audio spectrum analysis logic 116a proceeds to box 243.

Next, in box 243, the audio spectrum analysis logic 116a identifies substances 153 (FIG. 8) with resonant frequencies 154 falling within the frequency ranges 143. If the substance 153 has a resonant frequency 154 that falls within the frequency ranges, then the subject 103 (FIG. 1) has an imbalance associated with the substance 153. Thereafter, the audio spectrum analysis logic 116a proceeds to box 246.

In box 246, the audio spectrum analysis logic 116a identifies physiological profiles 169 potentially relevant to the subject 103 who produced the sound print(s) 113 for a list of physiological profiles 119. These physiological profiles 119 may be, for example, profiles of known medical conditions such as various diseases, addictions, and other conditions as described above. The physiological profiles 119 may include, for example, substances 163 most consistently found in a population of people suffering from the respective condition listed in the physiological profile 119. These substances 163 may be identified, for example, by taking samples of sound prints 113 from several subjects known to have such conditions. Alternatively, such information may be available in the literature. The relevancy of a physiological profile 119 to a given subject 103 may be determined, for example, by the number of substances 163 associated with the profile 119 that match substances 153 whose resonant frequencies 154 are found to fall within the frequency ranges 143 identified in the given sound prints 113. Thereafter, the audio spectrum analysis logic 116a proceeds to box 249.

Next, in box 249, the audio spectrum analysis logic 116a produces a report 123 containing the sub-reports 189 of the physiological profiles and the microorganism profiles 206 that are applicable to the subject 103. This report may contain, for example, only the most relevant physiological profiles.

In addition, there may be other functionality as described above that is not depicted in the flowchart of FIG. 12 that is executed in coordination with any manipulation of various components of the audio spectrum analysis application 116 as can be appreciated.

Although the flow chart of FIG. 12 shows a specific order of execution, it is understood that the order of execution may differ from that which is depicted. For example, the order of execution of two or more blocks may be scrambled relative to the order shown. In addition, two or more blocks shown in succession in FIG. 12 may be executed concurrently or with partial concurrence. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present invention.

Also, where the audio spectrum analysis application 116 is expressed in the form of software or code, it can be embodied in any computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present invention, a "computer-readable medium" can be any medium that can contain, store, or maintain the network page for use by or in connection with the instruction execution system. The computer readable medium can comprise any one of many physical media such as, for example, electronic, magnetic, optical, or semiconductor media. More specific examples of a suitable computer-readable medium would include, but are not limited to, magnetic tapes, magnetic floppy diskettes, magnetic hard drives, or compact discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Figure 13:
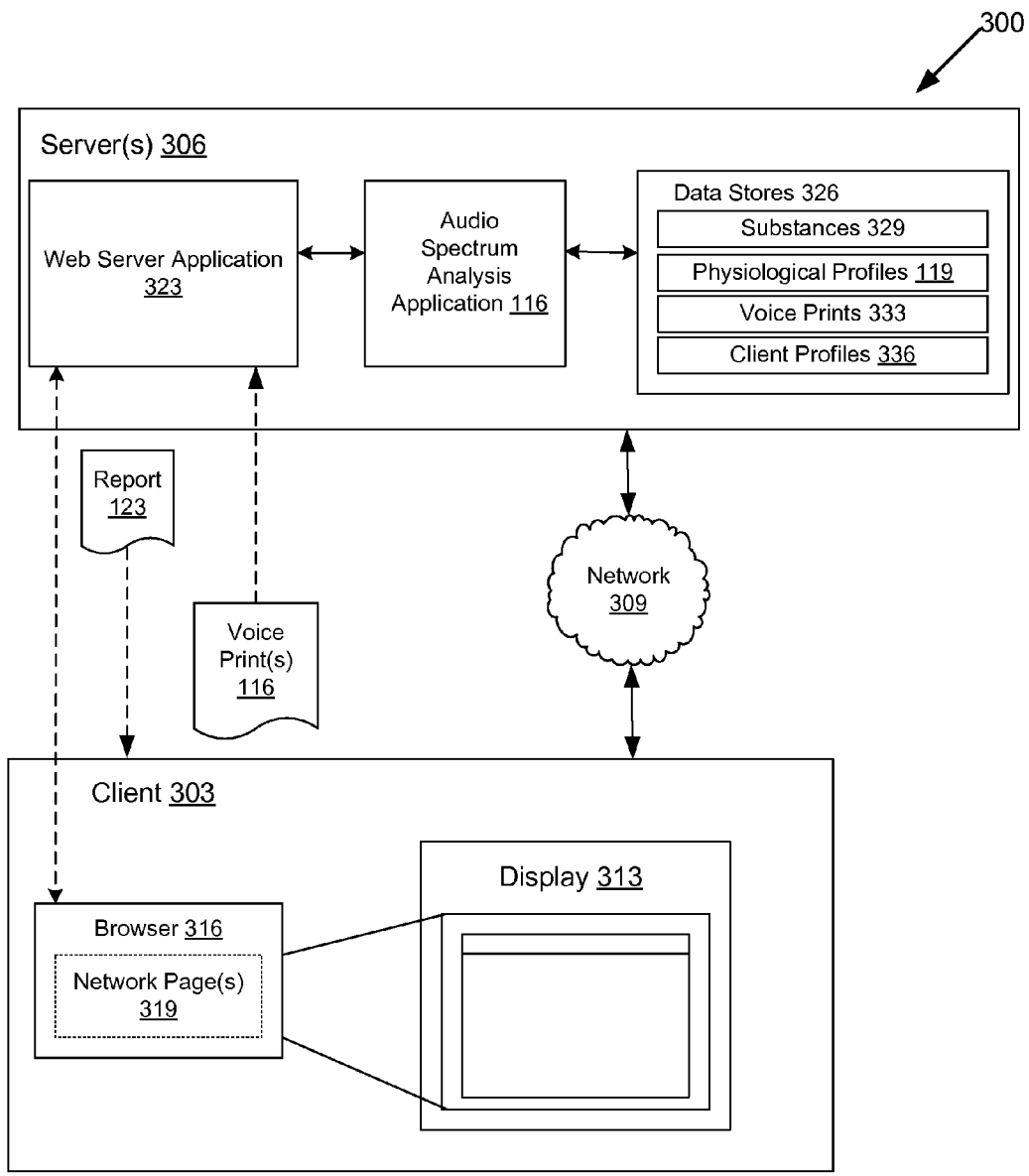
FIG. 13 is a block diagram of a networked sound diagnosis system according to an embodiment of the present invention.

With reference to FIG. 13, shown is an example implementation of the audio spectrum analysis application 116 according to an embodiment of the present invention. Shown is a sound diagnosis network 300 that includes a client 303 and a server 306. The client 303 and the server 306 each represent a plurality of servers/clients that may exist in the sound diagnosis network 300. The client 303 and the server 306 are each coupled to an appropriate network 309. The network 309 includes, for example, the Internet, intranets, wide area networks (WANs), local area networks, wireless networks, or other suitable networks, etc., or any combination of two or more such networks. The various components in the server(s) 306 are employed to facilitate the diagnosis of sound print(s) 113 using the audio spectrum analysis application 116 existing on the server 306 as will be described.

The client 303 may comprise, for example, a computer system such as a laptop, desktop, personal digital assistant, mobile telephone, or other handheld device with similar capability. The client 303 may include various input devices such as, for example, a keyboard and mouse. Alternatively, other input devices may be employed such as a keypad, touch pad, touch screen, microphone, scanner, joystick, or one or more push buttons, etc. The peripheral devices may also include the display device 313, indicator lights, speakers, printers, etc. The display device 313 may be, for example, cathode ray tubes (CRTs), liquid crystal display screens, gas plasma based flat panel displays, or other types of display devices, etc.

The client 303 also includes a browser 316 that is used to access a given network page 319 that is requested from the server 306. The network page 319 may be, for example, a dynamic network page such as a dynamic web page or other type of network page. For example, while navigating through the various network pages 319 made available through the server 306 so as to upload sound print(s) 113, the browser 316 may send a request for a specific network page 319 to the web server application 323. The web server application 323 will interface with the audio spectrum analysis application 116 to generate the desired network page that is then transmitted to the browser 316 of the client 303. Once the network page 319 is obtained, the browser 316 causes the network page 319 to be rendered on a display 313 of the client.

The server 306 may comprise multiple server computers that are typically referred to as "servers". Such servers may comprise computer systems that have been designed for running various server applications. The design of server computers accommodates handling the requests from multiple clients 303 as can be appreciated.

The server 306 includes various components that are executed in order to analyze the sound print(s) 113. To this end, the server 306 includes, for example, a web server application 323, an audio spectrum analysis application 116, and a data store 326. The web server application 323 serves up network pages that facilitate uploading of sound print(s) 113 from the client 303 to the server 306. According to one embodiment, the web server application 323 generates network page(s) 319 and provides browser access to the functions of the server 306 as determined by the audio spectrum analysis application 116. To this end, the web server application 323 acts as a gateway through which requests are received and responses transmitted to the client 303. It is understood that other applications and components may be executed on the server 306 beyond those described herein.

The audio spectrum analysis application 116 facilitates the diagnosis of the sound print(s) 113 and the generation of a report 123 that can be used to diagnose the subject 103 that provided the sound print(s) 113. The audio spectrum analysis application 116 may access the data store 326 to obtain lists of substances 329, physiological profiles 119, sound print(s) 333, and client profiles 336. As contemplated herein, the data store 326 may be representative of many different data stores included in a given system. The data store 326 may comprise, for example, a database or other data storage structure. Once the report 123 is generated by the audio spectrum analysis application 116, it is sent back to the client 303.

This embodiment has the advantage, among other advantages, of allowing subjects to record the sound prints 113 in local clinics or other medical facilities with a client 303 machine. These local clinics may then upload the sound prints 113 to a central facility hosting the server 303. Once the analysis has been performed, the central facility may download the report 123 to the local clinic. The clinic may then use the report 123 to make a diagnosis for the subject 103 and then prescribe courses of treatment for the subject 103.

Figure 14:
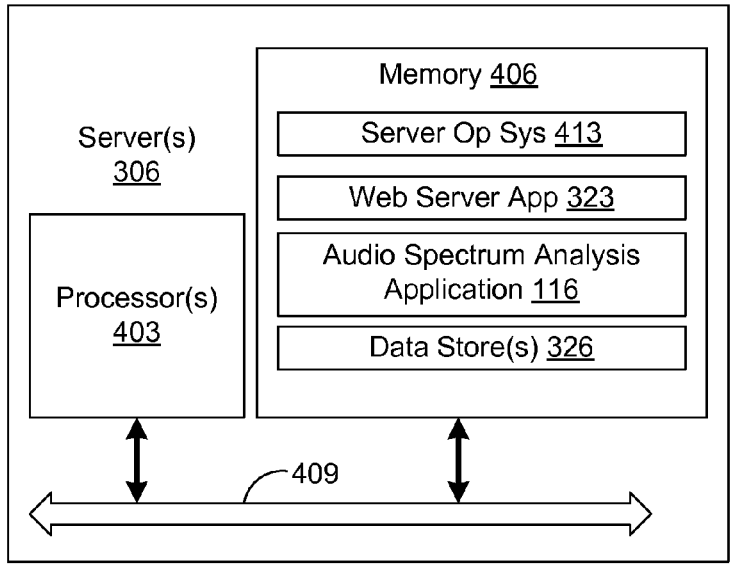
FIG. 14 is a schematic block diagram that illustrates one example of the server of FIG. 2 according to an embodiment of the present invention.

Next, with reference to FIG. 14, shown is one example of server 306 according to an embodiment of the present invention. The server 306 may include one or more processor circuits having a processor 403 and a memory 406, both of which are coupled to local interface 409. In this respect, the local interface may comprise, for example, a data bus with an accompanying control/address bus, as can be appreciated. The server 306 is one example of a server computer that may be employed as can be appreciated. Stored on the memory 406 and executable by the processor 403 are various components such as a server operating system 413, the web server application 323, and the audio spectrum analysis application 116. In addition, the data store 326 may be located in the memory 406 as can be appreciated. In addition, it is understood that many components may be stored in the memory 406 and executable by the processors 403.

Figure 15:
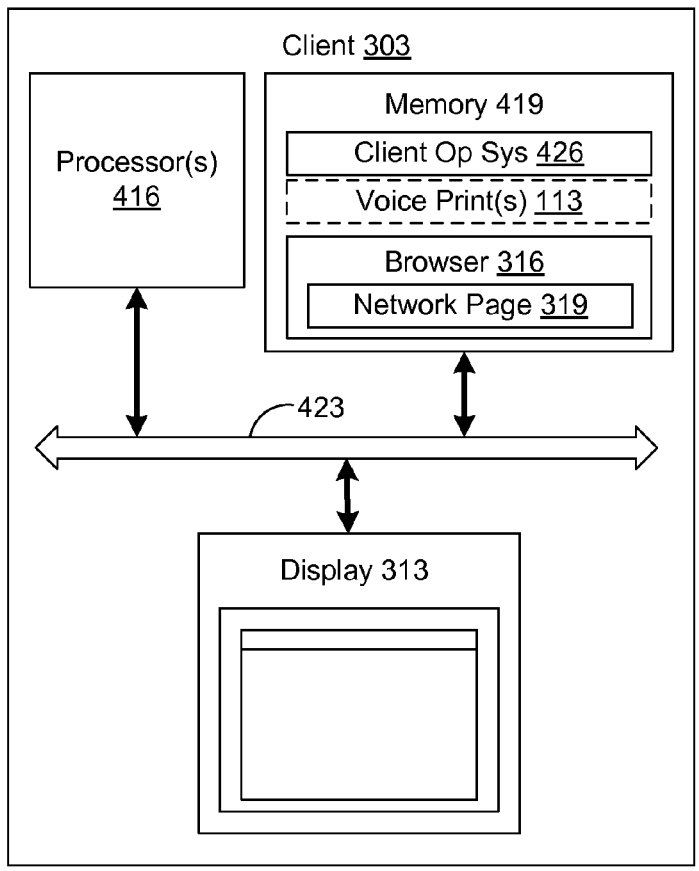
FIG. 15 is a schematic block diagram that illustrates one example of the client of FIG. 2 according to an embodiment of the present invention.

With reference to FIG. 15, shown is one example of a client 303 according to an embodiment of the present invention. As shown, the client 303 also includes a processor circuit having a processor 416 and a memory 419, both of which are coupled to a local interface 423. Stored in the memory 419 and executable by the processor 416 are the client operating system 426 and a browser 316. The browser 316 is executed to access and render the network pages 319 as described above. In addition, the client 303 includes the display device 313 upon which the network page 319 is rendered. As set forth above, with reference to both FIGS. 14 and 15, a number of components are stored in memories 406 and 419 and are executable by their respective processors 403 and 416. In this respect, the term "executable" refers to a program file that is in a form that can ultimately be run by the respective processors 403 and 416. Programs may be, for example, a compiled program that can be translated into machine code in a format that can be loaded into random access portions of the memories 406 and 419 and run by the processors.

Examples of executable programs may be, for example, a compiled program that can be translated into machine code in a format that can be loaded into a random access portion of the memories 406 and 419 and run by the processors 403 and 416, respectively, or source code that may be expressed in proper format such as object code that is capable of being loaded into a random access portion of memories 406 and 419 and executed by the processors 403 and 416, respectively. An executable program may be stored in any portion or component of the memories 406 and 419 including, for example, random access memory, read-only memory, a hard drive, compact disk (CD), floppy disk, or other memory components.

Each of the memories 406 and 419 is defined herein as both volatile and nonvolatile memory and data storage components. Volatile components are those that do not retain data values upon loss of power. Nonvolatile components are those that retain data upon a loss of power. Thus, each of the memories 406 and 419 may comprise, for example, random access memory (RAM), read-only memory (ROM), hard disk drives, floppy disks accessed via an associated floppy disk drive, compact discs accessed via a compact disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, each of the processors 403 and 416 may represent multiple processors and each of the memories 406 and 419 may represent multiple memories that operate in parallel processing circuits, respectively. In such a case, each of the local interfaces 409 and 423 may be an appropriate network that facilitates communication between any two of the multiple processors, between any processor and any of the memories, or between any two of the memories, etc. The processors 403 and 416 may be of electrical or optical construction, or of some other construction as can be appreciated by those with ordinary skill in the art.

The operating systems 413 and 426 are executed to control the allocation and usage of hardware resources such as the memory, processing time and peripheral devices in the server 306 and the client 303. In this manner, the operating systems 413 and 426 serve as the foundation on which applications depend as is generally known by those with ordinary skill in the art.

Although the functionality of the audio spectrum analysis application 116 is described as being embodied in software or code executed by general purpose hardware as discussed above, as an alternative the same may also be embodied in dedicated hardware or a combination of software/general purpose hardware and dedicated hardware. If embodied in dedicated hardware, the functionality of the network page 319 can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, programmable gate arrays (PGA), field programmable gate arrays (FPGA), or other components, etc. Such technologies are generally well known by those skilled in the art and, consequently, are not described in detail herein.

Figure 16:
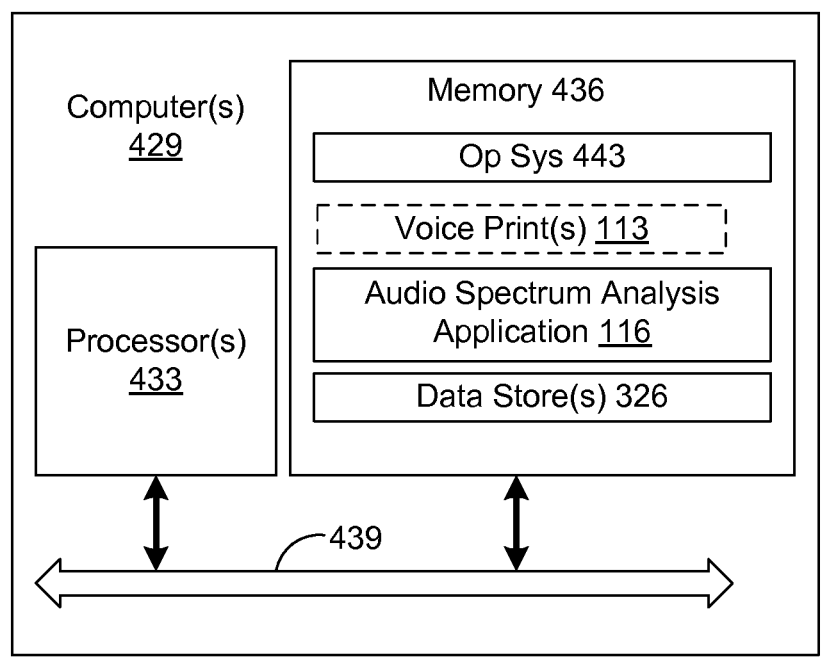
FIG. 16 is a schematic block diagram that illustrates one example of an implementation of the sound diagnosis system of FIG. 1 according to an embodiment of the present invention.

Next, with reference to FIG. 16, shown is one example of computer 429 according to an embodiment of the present invention. The computer 429 may include one or more processor circuits having a processor 433 and a memory 436, both of which are coupled to local interface 439. In this respect, the local interface may comprise, for example, a data bus with an accompanying control/address bus, as can be appreciated. The computer 429 is one example of a computer that may be employed as both the client computer and the server computer. Stored on the memory 436 and executable by the processor 433 are various components such as a operating system 443, the audio spectrum analysis application 116, and the sound prints 113. In addition, the data store 326 may be located in the memory 436 can be appreciated. In addition, it is understood that many components may be stored in the memory 436 and executable by the processors 433. In this embodiment, the system is self-contained. It could be located, for example, in a clinic or other medical facility.

The block diagrams, the flow chart, and/or the tables of FIGS. 1-16 show the architecture, functionality, and operation of an implementation of the audio spectrum analysis application 116. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor in a computer system or other system. The machine code may be converted from the source code, etc. If embodied in hardware, each block may represent a circuit or a number of interconnected circuits to implement the specified logical function(s).

Also, where any of the applications are expressed in the form of software or code, they can be embodied in any computer-readable medium for use by or in connection with an instruction execution system such as, for example, a processor in a computer system or other system. In this sense, the applications may comprise, for example, statements including instructions and declarations that can be fetched from the computer-readable medium and executed by the instruction execution system. In the context of the present invention, a "computer-readable medium" can be any medium that can contain, store, or maintain the network page for use by or in connection with the instruction execution system. The computer readable medium can comprise any one of many physical media such as, for example, electronic, magnetic, optical, or semiconductor media. More specific examples of a suitable computer-readable medium would include, but are not limited to, magnetic tapes, magnetic floppy diskettes, magnetic hard drives, or compact discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

It should be emphasized that the above-described embodiments of the present invention are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A method for sound analysis, comprising the steps of:
    transforming, in a computing device, a sound print into a frequency domain in a memory to generate a frequency spectrum;
    identifying, in the computing device, a plurality of signatures in the frequency spectrum, wherein the signatures each comprise a maximum amplitude shift that is less than a predefined threshold over a predefined frequency band;

identifying, in the computing device, a plurality of frequency ranges associated with the signatures in the sound print; and cross referencing, in the computing device, a plurality of frequencies associated with a profile with the frequency ranges to determine if the profile is applicable to the sound print.

2. The method of claim 1, wherein the step of transforming, in the computing device, the sound print into the frequency domain in the memory to generate the frequency spectrum further comprises the step of:

processing the sound print through a Frequency Transform.

3. The method of claim 1, wherein the step of identifying, in the computing device, the plurality of signatures further comprises the step of:

identifying, in the computing device, the signatures in the sound print by analyzing the sound print over a plurality of octaves.

4. The method of claim 1, wherein the signatures are substantial zero slopes.

5. The method of claim 1, further comprising:

generating, in the computing device, a prioritized list of the frequency ranges wherein the prioritized list of frequency ranges is prioritized by a magnitude of each of the frequency ranges.

6. The method of claim 1, wherein the step of cross referencing, in the computing device, the plurality of frequencies further comprises the step of:

cross referencing, in the computing device, a list of frequencies associated with the profile, where the profile is one of a plurality of profiles.

7. The method of claim 6, wherein the step of cross referencing the list of frequencies further comprises the step of:

determining if the profile is applicable to the sound print by a degree to which the frequencies associated with the profile fall within the frequency ranges.

8. A non-transitory computer-readable medium having a computer program executable on a computing device for sound analysis, comprising:

code that provides for transforming a sound print into a frequency domain to generate a frequency spectrum;

code that identifies a plurality of signatures in the frequency spectrum, wherein the signatures each comprise a maximum amplitude shift that is less than a predefined threshold over a predefined frequency band;

code that identifies a plurality of frequency ranges associated with the signatures in the sound print; and code that cross references a plurality of frequencies associated with a profile with the frequency ranges to determine if the profile is applicable to the sound print.

9. The non-transitory computer-readable medium of claim 8, wherein the code that provides for transforming the sound print into the frequency domain to generate the frequency spectrum further comprises a Fast Fourier Transform (FFT).

10. The non-transitory computer-readable medium of claim 8, wherein the code that identifies the plurality of signatures in the frequency spectrum further comprises:

code that identifies the signatures in the sound print by analyzing the sound print over a plurality of octaves.

11. The non-transitory computer-readable medium of claim 8, wherein the plurality of signatures are substantial zero slopes.

12. The non-transitory computer-readable medium of claim 8, further comprising:

code that generates a prioritized list of the frequency ranges wherein the prioritized list of frequency ranges is prioritized by a magnitude of each frequency range.

13. The non-transitory computer-readable medium of claim 8, wherein the code that cross references the plurality of frequencies associated with the profile with the frequency ranges further comprises:

code that cross references a list of frequencies associated with the profile, where the profile is one of a plurality of profiles.

14. A system, comprising:

a processor circuit having a processor and a memory;

a sound analysis system stored in the memory and executable by the processor, the sound analysis system comprising:

logic that provides for transforming a sound print into a frequency domain to generate a frequency spectrum;

logic that identifies a plurality of signatures in the frequency spectrum, wherein the signatures each comprise a maximum amplitude shift that is less than a predefined threshold over a predefined frequency band;

logic that associates a plurality of frequency ranges with the signatures in the sound print; and logic that cross references a plurality of frequencies associated with a profile with the frequency ranges to determine if the profile is applicable to the sound print.

15. The system of claim 14, wherein the sound analysis system further comprises a set of sound prints.

16. The system of claim 14, wherein the sound print is transformed into the frequency domain to generate the frequency spectrum over a plurality of octaves, wherein the signatures in the sound print are identified by analyzing the sound print over the plurality of octaves.

17. The system of claim 14, wherein the plurality of signatures are substantial zero slopes.

18. A method for signature identification, the method comprising the steps of:

identifying, in a computing device, a plurality of frequency measurement points within a frequency spectrum, the frequency spectrum being generated from a sound print;

measuring, in the computing device, an amplitude shift between consecutive ones of the frequency measurement points; and identifying, in the computing device, an existence of a signature in a frequency band in the frequency spectrum, the signature comprising a maximum amplitude shift that is less than a predetermined maximum amplitude shift over the frequency band.

19. The method of claim 18, wherein the frequency band has a width of at least 0.33Hz.

20. The method of claim 18, wherein the predetermined maximum amplitude shift is 0.15dB.

* * * * *